United States Patent
Aubert et al.

(10) Patent No.: US 6,190,671 B1
(45) Date of Patent: Feb. 20, 2001

(54) DRUG, PARTICULARLY AN IMMUNOMODULATOR, CONTAINING NON-FRUCTIFYING, NON-PHOTOSYNTHETIC FILAMENTOUS BACTERIA ENVELOPES OR FRACTIONS THEREOF, AND PREPARATION THEREOF

(75) Inventors: Lucien Aubert, Cap d'Ail; Richard Martin, Vouvray, both of (FR)

(73) Assignee: L'Oreal, Paris (FR)

( * ) Notice: Under 35 U.S.C. 154(b), the term of this patent shall be extended for 0 days.

(21) Appl. No.: 08/462,036

(22) Filed: Jun. 5, 1995

Related U.S. Application Data

(63) Continuation of application No. 08/211,031, filed on Jun. 29, 1994, now abandoned.

(30) Foreign Application Priority Data

Jul. 20, 1992 (FR) .................................................. 92 08932
Jul. 20, 1993 (WO) ................................. PCT/WO93/00741

(51) Int. Cl.$^7$ ........................... A61K 45/00; A01N 63/00
(52) U.S. Cl. ..................... 424/282.1; 424/93.4; 514/928; 514/885
(58) Field of Search ................................ 424/282.1, 93.4; 514/928, 885

(56) References Cited

U.S. PATENT DOCUMENTS

| | | | | |
|---|---|---|---|---|
| 4,419,449 | * | 12/1983 | Maillard et al. ...................... | 435/170 |
| 4,755,382 | * | 7/1988 | Flaherty ................................. | 424/92 |
| 4,978,622 | * | 12/1990 | Mishell et al. ........................ | 435/274 |
| 5,552,146 | * | 9/1996 | Hansen et al. ..................... | 424/251.1 |
| 5,889,049 | * | 3/1999 | Juergens ............................... | 514/510 |

FOREIGN PATENT DOCUMENTS

| | | | | |
|---|---|---|---|---|
| 0537277 | * | 3/1975 | (DE) ................................ | C12B/1/00 |
| 2034687 | | 6/1980 | (GB) . | |

OTHER PUBLICATIONS

Thompson et al, Biotechnol. Lett S(11): 761–766, 1483 (Abstract Only Enclosed).*
Cagle G. D., Can. J. Microbiol 21:395–408, 1975.*
Strohl et al, Int. J. of Systemic Biology 36(2): 302–313, 1986.*
Gialdroni—Grassi. Int. Archs Allergy. Appl. Immun. 76: Suppl 1, pp. 119–127, 1985.*
Rivas et al. An. R. Acad. Farm 41(4): 541–590, 1976 (Abstract).*
Strohl et al. International J. of Systematic Bacteriology 36(2): 302–313, 1986.*
Thompson et al. Biotechnology Letters 5(11): 761–66, 1983.*
Burton et al. J. Bacteriology 88:1755–1761, 1964.*
Flaherty et al. Infection and Immunity 43(1): 206–212, 1984.*
Webster's II. New Riverside University Dictionary p. 933.*
Brooks et al. Medical Microbiology, 20$^{th}$ ed. 1995 pp. 410–423.*
Dr. Michael Jacobs, "The Office Mangement of Obstructive Lung Disease," http://www.Med.Stanford.Edu/School/DGIM/Teaching/Modules/Copd. Html. Visited Jul. 13, 1999.*
Georgiou et al, "Identification of B, C, and D Cytochromes in the Membrane of Vitreoscilla", Biological Abstracts, vol. 85, 1988, Abstact No. 30874.
Roitt et al, Immunology, Mosby, 3rd Edition, pp. 15.17–15.18.
Brandtzaeg, ORL 50:225–235, 1988.
Ohashi et al, Acta Otolaryngol, (Stockh) 104:495–499, 1987.
Barbul, Clinics in Plastic Surgery, vol. 17, No. 3, Jul. 1990 pp. 433–442.
Mashihi et al, J. Immunopharmac., vol. 8, No. 3, pp. 339–345, 1986.
Gialdroni–Grassi et al, Int. Archs Allergy appl. Immun., 76: suppl. 1, pp. 119–127 (1985).
Georgiou et al, Arch. Microbiol. 148:328–333 (1987).

\* cited by examiner

*Primary Examiner*—Rodney P. Swartz
(74) *Attorney, Agent, or Firm*—Nixon & Vanderhye, P.C.

(57) ABSTRACT

A drug containing, in particular, fractions of the envelopes of bacteria of genera Beggiatoa and Vitreoscilla. The drug is particularly useful for treating ear, nose and throat infections or bronchopulmonary infections.

10 Claims, No Drawings

DRUG, PARTICULARLY AN IMMUNOMODULATOR, CONTAINING NON-FRUCTIFYING, NON-PHOTOSYNTHETIC FILAMENTOUS BACTERIA ENVELOPES OR FRACTIONS THEREOF, AND PREPARATION THEREOF

This is a continuation of Application Ser. No. 08/211,031, filed Jun. 29, 1994, now abandoned.

The subject of the invention is a new medicinal product containing, as active ingredient, envelopes or fractions of envelopes of non-photosynthetic and non-fruiting filamentous bacteria, as well as its preparation.

It is known that certain constituents of the envelopes of Gram-negative bacteria, and especially the lipopolysaccharide fractions which can be extracted therefrom, exhibit properties of non-specific stimulation of the immune defences of the body; see for example Int. Archs Allergy Appl. Immun. 76 Suppl. 1.119–127, (1985), and Journal of immunopharmacology 3(2), 119–132(1981).

It has now been discovered that the envelopes of certain bacteria called, according to the classification of Bergey's Manual, non-photosynthetic and non-fruiting filamentous bacteria, exhibit particularly advantageous immunomodulatory properties. They stimulate especially, in a non-specific manner, the immune defences, including cellular immunity and in particular the macrophages.

The subject of the invention is therefore a medicinal product having especially an immunomodulatory effect, containing bacteria envelopes or fractions of these envelopes, characterized by the fact that the said bacteria are chosen from the non-photosynthetic and non-fruiting filamentous bacteria as defined according to the classification of Bergey's Manual of Systematic Bacteriology, Volume 3, Section 23, 9th Edition 1989.

"Envelope" is called herein the bacterial wall and optionally the underlying membranes.

Among the bacteria whose envelopes or envelope fractions constitute an active ingredient of the immunomodulatory medicinal product of the invention, there may be mentioned more particularly the bacteria belonging to the order Beggiatoales, and especially the bacteria belonging to the genus Beggiatoa, such as for example various strains of Beggiatoa alba according to the definition given in Arch. Microbiol. (1984) 137,139–144. It should be noted that this definition of B. alba corresponds to the former names Beggiatoa arachnoidea, B. gigantea, B. leptomiformis, B. minima, B. mirabilis of Bergey's Manual, 8th Edition.

There may be mentioned, moreover, the bacteria belonging to the genus Vitreoscilla which is known to be related to and often difficult to differentiate from the genus Beggiatoa.

The bacteria which have just been defined, and of which several have already been described, generally have an aquatic habitat and can be found especially in thermal springs.

Among the bacteria which can be used there may be mentioned for example:

Vitreoscilla beggiatoïdes (ATCC 43181)

Beggiatoa alba (ATCC 33555).

It is known that the culture of non-photosynthetic and non-fruiting filamentous bacteria is relatively difficult, like the production of pure cultures. Most others recommend the use of poorly defined media, including various maceration fluids using tap water. The carbon source recommended is an acetate.

It has now been discovered that it is possible to adapt these bacteria, by counter-selection, to the use of a monosaccharide, instead of acetate, as carbon source.

It has been discovered, in addition, that it is possible to culture these bacteria on a perfectly defined culture medium. A culture can in particular be carried out in the following medium:

TABLE 1

| COMPOSITION | CONCENTRATION |
| --- | --- |
| Autolytic yeast extract | 0.5 to 5 g/l |
| Peptone | 0.5 to 5 g/l |
| Glucose, anhydrous | 0.5 to 7 g/l |
| Heller microelements | 0.5 to 5 ml/l |
| $CaCl_2.10H_2O$ | 0.010 to 0.200 g/l |

The mixture is adjusted to 1000 ml with distilled water. Among the peptones which can be used, may be mentioned for example soya bean papain peptone.

This special medium differs from the media generally used in the absence of catalase and sulphide.

The Heller microelements, of which the composition is given in the experimental section below, have been described by Heller, Ann Sci. Nat. Biol. Veg. 14:1–223 (1953). They are mixtures of various mineral elements which were recommended by Heller, not for the culture of bacteria but for the nutrition of plant tissues cultivated in vitro. It should be noted here that attempts were not made to determine if the Heller micro-elements are all essential or useful in the culture of non-photosynthetic and non-fruiting filamentous bacteria. It has nevertheless been found that the Heller microelements, when used together, for example in combination with the other constituents mentioned in Table 1 above, indeed permit the culture of the bacteria considered.

The culture can be performed at the appropriate temperature suitable for the cultured bacterial species. Generally, this temperature is between 18 and 40° C. according to the strains. The pH of the culture medium is preferably between 5.5 and 8.

By virtue of the process of the invention, it was possible to obtain, from samples of thermal springs, axenic cultures, in spite of the known difficulties of obtaining pure cultures of non-photosynthetic and non-fruiting filamentous bacteria.

The subject of the invention is therefore also a process for the culture, in aqueous medium, of non-photosynthetic and non-fruiting filamentous bacteria, mainly characterized by the fact that the culture is carried out using a monosaccharide, for example glucose, as main carbon source. Strains which have been adapted and selected, as indicated above, for the use of a monosaccharide, instead of acetate, as main carbon source, are therefore thus cultured. The culture can therefore be carried out in the absence of acetate. According to other embodiments, the procedure can, in addition, be carried out in the absence of $H_2S$ (or of sulphides) and/or in the absence of catalase, although these ingredients were generally considered as being essential up until now. The procedure can also be carried out in the presence of Heller microelements, for example in the proportions indicated in Table 1. The culture medium defined in Table 1 can be used in particular.

The subject of the invention is also a process for the preparation of a medicinal product as defined above, characterized by the fact that the said bacteria are cultured in an appropriate culture medium, and that the strains capable of multiplying using a monosaccharide as main carbon source are then selected and cultured, that the biomass or the bacterial envelopes are separated, and that fractions of the said envelopes, especially lipopolysaccharide fractions, are optionally extracted according to known methods.

When strains are used which have not yet been adapted, for example strains or mixtures of strains from a sample of thermal springs or of sea water, they are first cultured in a conventional culture medium containing acetate (for example sodium acetate) as sole carbon source. The strains capable of multiplying using a monosaccharide, for example glucose, as sole carbon source are then selected, in particular by culturing in the defined medium which was indicated earlier. For the selection and production of pure cultures, methods for the inoculation of solid culture media (agar gel) by means of dilutions of liquid culture media, are used in a known manner in order to isolate colonies derived from the same bacterial cell.

After culturing the bacteria, the biomass can be isolated by various known methods, for example by filtration, by coagulation with an alcohol (ethanol, isopropanol or isobutanol), by drying on a scraped prelayer (starch, diatomes and the like) cylinder, or by freeze-drying. A preliminary concentration, for example at 80° C. under reduced pressure, improves this separation.

An operation for disrupting the envelopes can be carried out, for example by the action of ultrasound. Extracts can, in addition, be prepared having an immunostimulant activity, especially by means of an alcohol such as ethanol or propanol.

Lipopolysaccharide extracts can also be prepared according to known methods; see for example Noris and Ribbons, Methods in Microbiology, Vol. 5B, Academic Press (1971). The method generally used is the well known so-called Westphal method (or a related method), which consists in carrying out the extraction with water-phenol mixtures at 65° C. The extract is then subjected to a dialysis in order to remove the phenol.

The subject of the invention is also a pharmaceutical composition characterized by the fact that it contains, as active ingredient, at least one medicinal product as defined above.

The composition of the invention contains the active ingredient at a concentration sufficient to permit the administration of effective doses with an acceptable volume of composition. Generally, the composition of the invention contains from 0.01 to 1% by weight of active ingredient (expressed by convention in weight of lipopolysaccharide) relative to the total weight of the composition.

The composition of the invention contains, in addition to the active ingredient, an appropriate excipient which permits its administration enterally, parenterally or locally.

The composition of the invention can be prepared according to the usual galenic methods.

It can be provided especially in the form of a solution or suspension in a suitable liquid pharmaceutical vehicle, including a vehicle and a packaging permitting administration as aerosol. The liquid composition can be subjected to a freeze-drying, and reconstituted at the time of use. The composition of the invention is especially a composition packaged in the form of oral or injectable suspensions, or for local application, or alternatively in the form of compositions packaged for nasal or conjunctival application.

The composition of the invention can also be provided for example in the form of hard gelatin capsules, tablets, powders, suppositories, gingival pastes, or creams.

The composition of the invention can be used especially as immunostimulant medicinal product, in man or in animals.

It can be administered for example parenterally (intraperitoneally, subcutaneously, intramuscularly, intravenously, percutaneously), orally, nasally, conjunctivally, rectally or perlingually.

It can also be used by local application, for example by means of tablets which disintegrate in the mouth, especially in the non-specific immunotherapy of diseases of the buccal cavities.

The usual dosage, expressed by convention in weight of lipopolysaccharide, may range for example from 1 $\mu$g to 100 $\mu$g/kg of body weight and per day, in one or several administrations, depending on the condition treated.

The medicinal product of the invention can be administered prophylactically, in the various cases above and in particular for the prevention of recurrent infections of the otorhinolaryngological sphere (ENT), and for the prevention of infectious risks in chronic patients.

The galenic forms permitting application on the skin, for example creams, can be used in the treatment of burns and superficial sores. They have, in addition, cicatrisant properties.

The medicinal product of the invention is administered especially as immunostimulant treatment, in the ENT or bronchopulmonary domain or in the dermatological domain, in the case of bacterial, fungal or viral infections. Thus, when the medicinal product is used in the treatment of ENT or bronchopulmonary infections (rhinopharyngitis, laryngitis, sinusitis, angina, otitis, bronchitis and the like), it can be administered orally in the form of tablets containing for example 0.05 to 2 mg of active ingredient, or in the form of an injectable composition, for example in the form of a sterile ampule containing 0.01 mg to 0.05 mg of active ingredient or alternatively in the form of an aerosol composition containing for example 1 to 5 mg of active ingredient per 10 ml (and this for 200 doses). When the medicinal product is used in the treatment of dermatological conditions such as burns, sores, ulcers or eschars, it is generally used in the form of a cream or a gel containing 0.01 to 1% active ingredient.

The subject of the invention is also the use of whole bacteria or bacterial envelopes or fractions of the said envelopes (in particular lipopolysaccharide fractions) in the preparation of an immunostimulant or cicatrisant medicinal product, this use being characterized by the fact that the said bacteria are chosen from non-photosynthetic and non-fruiting filamentous bacteria as defined above.

The following examples illustrate the invention without, however, limiting it.

EXAMPLE 1

Selection/adaptation of a Non-photosynthetic and Non-fruiting Filamentous Bacterium: Pharmacological Activity Following a sampling of a thermal spring from the Saint-Thomas spring, Oriental Pyrenees (France), various microbial cultures were carried out, using sodium acetate as carbon source.

These first cultures were carried out under the usual conditions for the identification of microorganisms in water, the culture temperature being 26° C.

Starting with bacterial colonies isolated by exhaustion on agar medium, the bacteria were selected in pure cultures capable of adapting to multiplication in a medium containing glucose as main carbon source.

The following culture medium was used (Table 2):

TABLE 2

| COMPOSITION | CONCENTRATION |
|---|---|
| Autolytic yeast extract Biokar (Ref. 112002) | 2 g/l |
| Soya bean papain peptone (origin PPS-USP Biokar Ref. 11601) | 2 g/l |
| Heller microelements | 2 ml/l |
| Glucose, anhydrous | 2 g/l |
| $CaCl_2.10H_2O$ | 0.066 g/l |
| Distilled water | 100 ml |

The pH is adjusted to 7.15 by addition of 1N sodium hydroxide or potassium hydroxide before sterilization at 121° C. for 20 minutes.

The composition of the Heller microelements, per 1l of distilled water, is the following:

| | |
|---|---|
| $ZnSO_4.7H_2O$ | 1 g |
| $MnSO_4.H_2O$ | 0.076 g |
| $CuSO_4.5H_2O$ | 0.003 g |
| KI | 0.010 g |
| $H_3BO_3$ | 1 g |
| $AlCl_3.6HO$ | 0.050 g |
| $NiCl_2.6H_2O$ | 0.030 g |

It was thus possible to select various strains of non-photosynthetic and non-fruiting filamentous bacteria. The characteristics of a filamentous bacterium which was thus isolated is described below:

Filaments (trichomes) 2–3 µm in diameter containing cells separated by septa, production of hormogonia, beige-white color in culture, isolated biomass of pink color, aerobic, Gram-negative, not requiring catalase, poly-β-hydroxybutyrate inclusions These characteristics do not permit, with the current techniques and bacterial taxonomy, to classify this strain which is at the interface of the two genera Beggiatoa and Vitreoscilla. It is known that these genera are very similar.

This strain can be preserved by direct freezing of the culture at the exponential growth phase, at −80° C. The strain can be thawed on a water bath at 37° C.

After several subcultures in solid medium, the strain adapted to the medium indicated above was stabilized.

Culture in glucose-containing liquid medium makes it possible to obtain perfectly distinct filaments whereas culture in acetate medium tends to give aggregates.

The optimum culture temperature is between 26 and 30° C.

Maintenance is ensured by subculturing at 48 h in the same liquid medium, using 1% of the total volume as inoculum.

Culture in a Fermenter

This culture is carried out in a stirred (200 revolutions/minute) and aerated 600 l fermenter.

The culture medium is that indicated above, with addition of 0.2 g/l of a polymethylsiloxane-type antifoam (SILBIONE 97350 RP). The temperature is regulated between 26 and 30° C., the optimum being at 29° C.

A complete growth cycle occurs in about 48 h. The yield achieved is of the order of 1.4 g of dry weight per liter.

The aeration is regulated by a mass flowmeter to have a minimum of 20% dissolved oxygen.

There is practically no residual glucose at the end of growth.

The biomass is harvested by centrifugation.

The procedure is carried out in an industrial type centrifuge cooled to 20° C. and capable of providing an acceleration greater than 5000×g. The biomass thus obtained can be heated at 121° C. for 20 min. This treatment breaks the cellular envelope and liberates the lipopolysaccharides. A crude extract is thus obtained which can be directly used and which can, if necessary, be purified by the Westphal method mentioned above.

Detection of the Immunoregulatory Activity on Human Macrophages in Culture:

The principle used is the following: when an immunomodulatory substance is introduced into a culture of human macrophages, an activation of the system can be observed by measuring the cytosolic free $Ca^{++}$, whose elevation corresponds to an activation of the macrophages. The cytosolic calcium level is measured by fluorescence by means of the INDO-1 probe in the form of an ester. The probe penetrates into the cells or is converted, under the action of esterases, into a calcium-binding form, the formation of a complex with the calcium ions being accompanied by a shift in the emission spectrum.

A human myelomonocytic leukaemic line THP1, provided by Dr. Matsushima, (National Cancer Institute, Fredericks, MD, USA), produced in an RPMI 1640 medium (GIBCO BRL FRANCE) supplemented with 5% (V/V) decomplemented foetal calf serum (SIGMA, FRANCE), 2 mM glutamine, 1 mM sodium pyruvate, 50 U/ml penicillin and 50 U/ml of streptomycin, is used.

The active ingredient studied, consisting of the extract obtained above, is introduced at various concentrations and incubated for 45 minutes in the dark. The macrophages ($5 \times 10^6$ cells/ml) are subjected to a 45 min incubation at 37° C. in the dark in the presence of 4 mM of the INDO-1 AM probe (in the form of an ester), marketed by France Biochem, in a medium composed of 140 mM Nacl, 5 mM KCl, 1 ml $CaCl_2$, 1 mM $MgCl_2$ 10 mM glucose, 20 mM HEPES, 0.1% bovine serum albumin, pH 7.4. The cells are then washed and resuspended at a concentration of $10^6$ cells/ml in the same medium.

The fluorescence is measured by means of a PERKIN-ELMER LS.5B® spectrofluorimeter at an emission wavelength of 410 nm for an excitation wavelength of 331 nm.

It is observed that the active ingredient studied increases the concentration of cytosolic $Ca^{++}$, this increase rising with the concentration of active ingredient which varies from 33 to 267 µg/ml.

The activation of macrophages can also be determined by measuring the mobilization of the intracellular calcium pool. This estimation is made after addition of the INDO-1® probe. The extracellular calcium is then chelated by EGTA (1 mM). The active ingredient studied is then added at various concentrations. After stabilization of the signal, the extracellular calcium concentration is restored by addition of $CaCl_2$ (2 mM) to the incubation medium.

It is observed that the active ingredient studied, at concentrations of 33 to 267 µg/ml, permits a liberation of the intracellular $Ca^{++}$ pool.

Measurement of the Production of Interleukin 1β

It is known that the secretion of IL1β by monocytic lines can be brought about by means of a variety of stimuli, especially chemical stimuli by means of phorbol esters (PMA).

The THP1 cells are incubated in the absence or in the presence of 1 or 2 ng/ml of PMA and varying concentrations of the active ingredient studied (varying from 10 to 100 μg/ml), for 24 h at 37° C. The secretion of IL1β is measured in the culture supernatant by means of an ELISA assay, using polypropylene plates (immulon 2 Dynatech). Anti-IL1β sheep immunoglobulins (IgG) are immobilized on the walls of the wells. The revealing is performed by means of Fab' fragments of anti-interleukin 1β antibodies, coupled with peroxidase. The reading is carried out by measuring the optical density at 492 nm, in the presence of ortho-phenylenediamine, by comparison with a standard curve obtained by means of recombinant IL1β.

The results are the following (Table 3):

TABLE 3

|  | Active Ingredient Concentration | | | |
| --- | --- | --- | --- | --- |
|  | 10 μg/ml | 100 μg/ml | 10 μg/ml | 100 μg/ml |
| IL1 production ng/ml | 0.2 | 1.0 | 15 | 100 |
| PMA concentration ng/ml | — | — | 1 | 2 |

In conclusion, the active ingredient studied stimulates the flow of $Ca^{++}$ in the macrophages. The effect is rapid (less than 2 seconds) and is dose-dependent. It affects both the flow of $Ca^{++}$ and the mobilization of the intracellular reserves. Furthermore, the active ingredient studied stimulates the production of IL1β after 24 h of incubation, which shows the absence of toxicity for the macrophages.

Cicatrisant Activity

Epidermal cicatrization:

On a depilated guinea pig, it is possible to induce by suction (depression of 120 mm of mercury for two hours) two purely epidermal sores of identical size. One of the sores can then be treated with the product to be studied, the other serving as control.

The products studied are applied in the form of a cream containing 1% of the extract prepared in Example 1, immediately after cutting the suction bubble (0.5 cm$^2$), in an occlusive dressing, in an amount of 10 mg/cm$^2$ of sore.

After 24 hours, fragments of skin bearing cicatrices are removed. After separation of the dermis and the epidermis by the action of sodium bromide, the size of the sore is measured on the separated epidermis, by planimetry.

The activity is expressed as percentage of reduction of the initial surface of the sore.

A reduction of 72% of the initial surface of the sore is observed whereas in the control area, the surface reduction is only 49% (mean of 12 measurements).

In another experiment, an epidermal sore was brought about by incision of the guinea pig's pad. The sores undergo three treatments, immediately after incision, then after 24 hours and 48 hours. After application, the sores are covered with an occlusive dressing. 24 hours after the last treatment, the skin of the paws is removed and the epidermis bearing the cicatrization is separated from the dermis by the action of sodium bromide. After rinsing, the breaking stress for the cicatricial epidermis is measured by means of an extensiometer of INSTRON brand.

For the treated cicatrices, the breaking stress (mean for 9 animals per product) is 139.8±23.66 Newton, whereas in the controls, the breaking stress is 63.2±6.14 Newton.

Dermal cicatrization in Rats

Incisions affecting the entire thickness of the dorsal skin are made in a standard manner.

The product studied is applied in the form of a cream, as above, in an amount of 10 mg/cm$^2$ (daily) on days D+5 to D+9 after incision, without dressing.

As above, the breaking stresses are measured for the total cicatricial skin excised on D+12. With the product studied at a concentration of 1%, the breaking stress is 428.4 Newton (mean for 9 animals per product) whereas the breaking stress for the control area is 290.4 Newton.

EXAMPLE 2

Skin Composition in the Form of a Cream

A cream having the following composition was prepared:

| | |
| --- | --- |
| Bacterial extract obtained according to the preparation process of Example 1 | 0.3 g |
| Vaseline oil | 20 g |
| Stearic acid | 3 g |
| Cetyl alcohol | 3 g |
| Polyethylene glycol stearate at 100 EO | 5 g |
| Propylene glycol | 3 g |
| Preservative | 0.3 g |
| Purified water qs | 100 g |

This cream is applied at a rate of three applications per day for 10 to 15 days on burns or sores, in order to accelerate cicatrization.

EXAMPLE 3

Injectable Solution

An injectable solution was prepared in the form of a unit dose having the following composition:

Bacterial extract obtained according to the preparation process of Example 1 0.03 g Sodium chloride at 0.8% in water 1 ml This injectable solution is used in the treatment of ENT or chronic bronchopulmonary conditions. The dosage is 1 deep subcutaneous injection starting with half a dose then one dose every 15 days for 2 months.

What is claimed is:

1. A method of stimulating non-specific immunity for preventing or treating otorhinolaryngological or bronchopulmonary infections comprising administering orally, nasally, rectally, perlingually or by injection, to a human in need of such treatment a composition containing at least one envelope of a bacteria or a lipopolysaccharide containing fraction of said envelope as an active agent in a pharmaceutically acceptable vehicle, said bacteria being selected form the group consisting of bacteria belonging to the order Beggiatoales and bacteria belonging to the genus Vitreoscilla.

2. A method of stimulating non-specific immunity in a human or animal in need of such treatment, comprising administering orally, nasally, rectally, perlingually or by injection, to said human or animal a composition containing at least one envelope of a bacteria or a lipopolysaccharide containing fraction of said envelope, as an active agent, in a pharmaceutically acceptable vehicle, said bacteria being selected from the group consisting of bacteria belonging to the order Beggiatoales and bacteria belonging to the genus Vitreoscilla.

3. The method according to claim 2, wherein said fraction of said envelope contains lipopolysaccharides of said bacteria.

4. The method of claim 2, wherein said composition is administered orally in the form of tablets containing 0.05 to 2 mg of said active agent.

5. The method of claim 2, wherein said composition is in the form of an injectable composition containing from 0.01 to 0.05 mg of said active agent.

6. The method of claim 2, wherein said composition is in the form of an aerosol composition containing 1 to 5 mg of said active agent per 10 ml.

7. A method of stimulating non-specific immunity for preventing or treating otorhinolaryngological or bronchopulmonary infections comprising administering to a human in need of such treatment a composition containing at least one envelope of a bacteria or a lipopolysaccharide containing fraction of said envelope as an active agent in a pharmaceutically acceptable vehicle, said bacteria being selected from the group consisting of bacteria belonging to the order Beggiatoales and bacteria belonging to the genus Vitreoscilla, wherein said composition is in the form of a tablet which disintegrates in the mouth, for local application, or in the form of an injectable composition.

8. A method of stimulating non-specific immunity in a human or animal in need of such treatment, comprising administering to said human or animal a composition containing at least one envelope of a bacteria or a lipopolysaccharide containing fraction of said envelope, as an active agent, in a pharmaceutically acceptable vehicle, said bacteria being selected from the group consisting of bacteria belonging to the order Beggiatoales and bacteria belonging to the genus Vitreoscilla, wherein said composition is in the form of a tablet which disintegrates in the mouth, for local application, or in the form of an injectable composition.

9. The method of claim 1 wherein said bacteria belongs to the genus Vitreoscilla.

10. The method of claim 2 wherein said bacteria belongs to the genus Vitreoscilla.

* * * * *